United States Patent [19]

Simon et al.

[11] Patent Number: 5,667,794
[45] Date of Patent: Sep. 16, 1997

[54] HEARTBURN TREATMENT

[75] Inventors: Thomas Simon, Berwyn; Roger Berlin, Haverford, both of Pa.

[73] Assignee: Merck & Co., Inc., Rahway, N.J.

[21] Appl. No.: 710,078

[22] Filed: Sep. 11, 1996

Related U.S. Application Data

[63] Continuation of Ser. No. 432,743, May 2, 1995, abandoned.
[51] Int. Cl.⁶ ........................................... A61K 33/00
[52] U.S. Cl. ..................... 424/401; 424/464; 424/687; 424/690; 424/692
[58] Field of Search ............................ 424/464, 687, 424/690, 692, 401; 514/819

[56] References Cited

U.S. PATENT DOCUMENTS

| | | |
|---|---|---|
| 4,283,408 | 8/1981 | Hirata et al. |
| 5,229,137 | 7/1993 | Wolfe ............................ 424/687 |

FOREIGN PATENT DOCUMENTS 0 492 247 A1  9/1991  European Pat. Off.

OTHER PUBLICATIONS

Pepcid AC Acid Control Product Monograph (published 1994).

"The Liberator . . ." (The Pharmaceutical Journal, May 7, 1994).

Chremos, A. N., "Clinical Pharmacology of Famotidine: A Summary", J. Clin. Gastroenterol, vol.9(Suppl. 2), pp. 7–12 (1987).

Thompson, et al., "Heartburn and globus in apparently healthy people", CMA Journal, vol. 126, pp. 46–48 (1982).

Laskin, et al., "Pharmacodynamics and Dose–Response Relationship of Famotidine: A Double–Blind Randomized Placebo–Controlled Trial", J. Clin. Pharmacol, vol. 33, pp. 636–639 (1993).

McCallum et al., "MK–208, A Novel Histamine H2–Receptor Inhibitor with Prolonged Antisecretory Effect", Digestive Diseases and Sciences, vol. 30, pp. 1139–1144 (1985).

Gitlin et al., "A Multiclinic Double–Blind Dose Ranging Study Evaluating the Efficacy and Safety of Famotidine in the Healing of Active Duodenal Ulcer as compared to Placebo", Amer. Journal of Gastroenterology, vol. 80, p. 840 (1985).

Miyoshi et al., "Clinical Evaluation of Famotidine on Acute Gastric Mucosal Lesions Associated with Acute Gastritis and Chronic Gastritis–Dose Finding Study by the Double Blind Comparative Method–", Naika Hokan, vol. 34, pp. 442–457 (1987).

Douds, Andrew C. and J. Douglas Maxwell, "Over the counter H2 receptor antagonists", BMJ, (Letters) vol. 309, p. 1156 (1994).

Cooper, J.R.B., "Increase the risks to offshore workers", BMJ, (Letters), vol. 309, pp. 1156–1157 (1994).

(List continued on next page.)

*Primary Examiner*—Thurman K. Page
*Assistant Examiner*—Sharon Howard
*Attorney, Agent, or Firm*—Richard S. Parr; Mel Winokur

[57] ABSTRACT

A method for treating a patient suffering from heartburn and having no substantial esophageal erosion, comprising administering to the patient a composition comprising an amount of famotidine between about 5 mg and 10 mg. In one embodiment, the amount of famotidine is about 5 mg. In another embodiment, the amount of famotidine is about 10 mg.

A method for treating a patient suffering from heartburn and having no substantial esophageal erosion, comprising administering to the patient a composition comprising an amount of famotidine between about 5 mg and 10 mg, and an antacid. In one embodiment, the amount of famotidine is about 5 mg. In another embodiment, the amount of famotidine is about 10 mg.

3 Claims, 1 Drawing Sheet

OTHER PUBLICATIONS

Simon et al., "Self–Directed Treatment of Intermittent Heartburn: A Randomized, Multicenter, Double–Blind(DB), Placebo(P)–Controlled Evaluation of Famotidine(FAM) 5, 10 & 20MG and Antacid(AA)", Esophageal, Gastric, and Duodenal Disorders, p. A181 (1994).

MSD Merck Sharp & Dohme, "PEPCID Insert".

F–D–C Reports—"The Tan Sheet" pp. 9–11, Apr. 18, 1994.

HEARTBURN TREATMENT

This is a continuation of application Ser. No. 08/432,743 filed on May 2, 1995, now abandoned.

BACKGROUND OF THE INVENTION

Heartburn, or pyrosis, is a sensation of pain or burning located substernally or high in the epigastrium with radiation into the neck and occasionally to the arms, associated with regurgitation of acid-peptic gastric juice into the esophagus. Occassional heartburn is common in normal persons, but frequent and severe heartburn is generally a manifestation of esophageal dysfunction. Heartburn may result from abnormal motor activity or distention of the esophagus relfux of acid or bile into the esophagus, or direct esophageal mucosa irritation (esophagitis).

Heartburn is most often associated with gastroesophageal reflux. In this setting, heartburn typically occurs after a meal, with stooping or bending, or when the patient is supine. It may be accompanied by the spontaneous appearance in the mouth of fluid which may be salty, sour, or bitter and green or yellow. Heartburn may arise following the ingestion of certain foods (e.g. citrus fruit juices) or drugs (e.g. alcohol or aspirin). Characteristically, heartburn is alleviated promptly, even if only temporarily, by antacids.

Heartburn may also occur in the absence of a demonstrated anatomic or physiologic condition. In this setting, it is frequently accompanied by aerophagia, which may represent an attempt by the patient to relieve discomfort, and is often attributed to psychological factors for lack of other explanations.

Reflux esophagitis consists of esophageal mucosal damage resulting from reflux of gastric or intestinal contents into the esophagus. Esophagitis, an inflammation of the esophagus from regurgitation of acid gastric contents, producing substernal pain, develops when the mucosal defenses that normally counteract the effect of injurious agents on the esophageal mucosa succumb to the onslaught of the refluxed acid pepsin or bile. Mild esophagitis shows microscopic changes of mucosal infiltration with granulocytes or eosinophils, hyperplasia of basal cells, and elongation of dermal pegs. Erosive esophagitis shows endoscopically visible damage to the mucosa in the form of marked redness, friability, bleeding, superficial linear ulcers, and exudates.

Famotidine (available from Merck & Co., Inc., Whitehouse Station, N.J., under the name PEPCID®), is an antagonist of the histamine $H_2$ receptor, is 3-{{{2-[(aminoiminomethyl) amino]-4-thiazolyl]methyl]thio]-N-(aminosulfonyl)propanimidamide, having the structural formula:

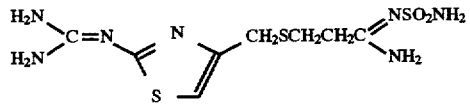

The primary clinically important pharmacologic activity of famotidine is inhibition of gastric secretion. Both acid concentration and volume of gastric secretion are reduced by famotidine. Famotidine is used to treat acid-related disorders such as gastric and duodenal ulcer, gastroesophageal reflux disease and Zollinger Ellison syndrome. Its safety and efficacy have been well established in controlled clinical studies, and use by over 31 million patients worldwide.

Studies of oral administration have shown that the onset of antisecretary effect occurs within one hour, and that the maximum effect, occurring within 1 to 3 hours, was dose dependent.

Single evening doses of 20 and 40 mg were shown to inhibit mean nocturnal gastric secretion by 86% and 94% respectively, for a period of 10 hours. The same doses, given in the morning, suppressed food stimulated acid secretion by 76% and 84%, respectively, 3 to 5 hours after administration, and 25% and 30%, respectively, 8 to 10 hours after administration. In some subjects who received 20 mg dose, the antisecretory effect was dissipated within 6 to 8 hours.

Trials have shown famotidine to be beneficial in a dose dependent manner in relief of symptoms associated with ulcerations and gastritis.

Gitlin et al., Amer. Journal of Gastroenterology (1985) vol. 80 pp. 840 examines famotidine efficacy in the treatment of active duodenal ulcers. The results suggest that duodenal ulcer healing rates are famotidine dosage dependent. 20 mg twice daily, 40 mg twice daily and 40 mg at bedtime were administered over a four week period. Healing rates of 67, 75, 70%, respectively, were seen.

Similarly, Miyoshi et al., Naika Hokan (1987) vol. 34 pp. 442–457 demonstrates that the efficacy of famotidine as a gastritis therapy is dose-related. Miyoshi et al. evaluated dosage regimens of 5, 10, or 20 mg twice daily in the treatment of gastritis symptom relief. Patients treated with 10 to 20 mg of famotidine had fewer erosions and mucosal haemorrhages than those treated with 5 mg famotidine.

McCallum et al., Dig. Dis. Sci. (1985) vol. 30 pp. 1139–1144 describes a study of healthy patients demonstrating that 5 mg of famotidine produces has an effect on gastric acid secretion. Laskin et al., J. Clin. Pharmacol. (1993) vol. 33 pp. 636–639 describes a study demonstrating that single doses of 5 and 10 mg of famotidine produces statistically significant decreases in intragastric acidity, beginning at 90–100 minutes and persisting for approximately 9 hours. Neither study measured the effects of 5 mg or 10 mg doses of famotidine on patients having pyrosis without esophagitis or pyrsosis with esophagitis.

Applicants have now administered doses of 5 mg, 10 mg, and 20 mg to patients suffering from heartburn without esophagitis (showing no substantial esophageal erosion), and to patients suffering from heartburn with esophagitis (showing substantial esophageal erosion). Applicants have found that the success in treating patients suffering from heartburn without esophagitis is not dose dependent, i.e., the benefit achieved by administering a 5 mg dose of famotidine to patients suffering from heartburn without esophagitis is substantially the same as the benefit achieved by administering a 10 mg dose, and that the benefit achieved by administering a 10 mg dose of famotidine to patients suffering from heartburn without esophagitis is substantially the same as the benefit achieved by administering a 20 mg dose of famotidine.

SUMMARY OF THE INVENTION

The invention is a method for treating a patient suffering from heartburn and having no substantial esophageal erosion, comprising administering to the patient a composition comprising an amount of famotidine between about 5 mg and 10 mg. The invention is also a method for treating a patient suffering from heartburn and having no substantial esophageal erosion, comprising administering to the patient a composition comprising an amount of famotidine between about 5 mg and 10 mg, and an antacid

DETAILED DESCRIPTION OF THE DRAWINGS

Figure 1B:
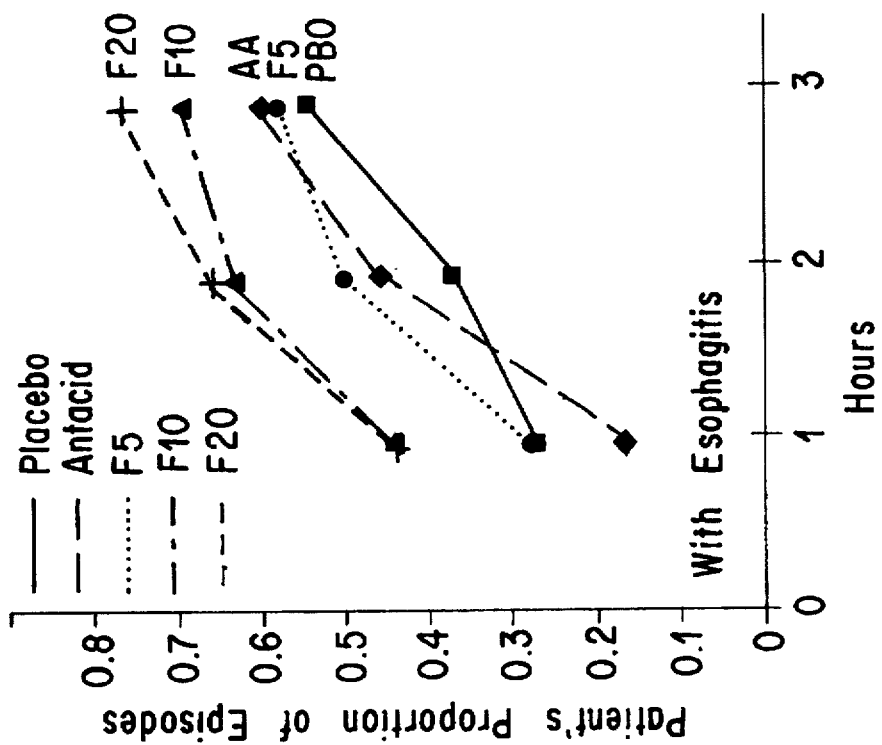
Figure 1A:
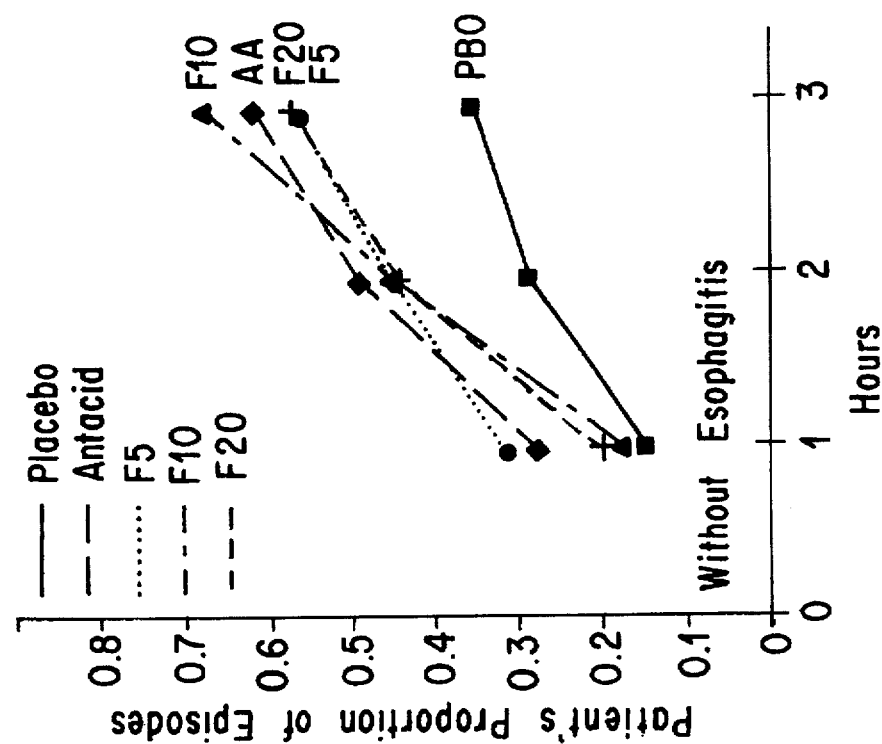

FIG. 1A is a graph representing heartburn patient response to treatment with famotidine 5 mg, famotidine 10 mg, famotidine 20 mg, antacid or placebo, for patients without esophagitis.

FIG. 1B is a graph representing heartburn patient response to treatment with famotidine 5 mg, famotidine 10 mg, famotidine 20 mg, antacid or placebo, for patients with esophagitis.

DETAILED DESCRIPTION OF THE INVENTION

The invention is a method for treating a patient suffering from heartburn and having no substantial esophageal erosion, comprising administering to the patient a composition comprising an amount of famotidine between about 5 mg and 10 mg. In one embodiment, the amount of famotidine is about 5 mg. In another embodiment, the amount of famotidine is about 10 mg.

The invention is also a method for treating a patient suffering from heartburn and having no substantial esophageal erosion, comprising administering to the patient a composition comprising an amount of famotidine between about 5 mg and 10 mg, and an antacid(s). In one embodiment, the amount of famotidine is about 5 mg. In another embodiment, the amount of famotidine is about 10 mg.

As described in the following example, applicants administered doses of 5 mg, 10 mg, and 20 mg of famotidine to patients suffering from heartburn without esophagitis (showing no substantial esophageal erosion), and to patients suffering from heartburn with esophagitis (showing substantial esophageal erosion) and evaluated the effect of these treatments in relieving heartburn episodes. Applicants have found that the success in treating patients suffering from heartburn without esophagitis is not dose dependent, i.e., the benefit achieved by administering a 5 mg dose of famotidine to patients suffering from heartburn without esophagitis is substantially the same as the benefit achieved by administering 10 mg or 20 mg doses of famotidine.

Antacids may optionally be administered with famotidine in order to relieve patients of heartburn symptoms. The antacids are typically selected from aluminum hydroxide, magnesium hydroxide, magnesium carbonate, magnesium oxide, magnesium aluminum silicate, magnesium trisilicate, sodium bicarbonate, calcium carbonate, bismuth carbonate, alkali metal salts of citric, tartaric, benzoic, sorbic and phosphoric acid, and combinations thereof, and co-dried gels, for example aluminum hydroxide-magnesium carbonate co-dried gel. A particular antacid is aluminum hydroxide or a mixture of aluminum hydroxide and magnesium hydroxide. In general, a dosage form contains between 5 mEq and 60 mEq of antacid, more particularly, between 10 mEq and 15 mEq of antacid.

Compositions for use in the present inventions may also contain pharmaceutically acceptable carriers. Compositions may be formulated for oral administration in solid or liquid form, for example as effervescent or non-effervescent powders or tablets, capsules, suspensions or dispersions. Compositions may thus be formulated by admixture with pharmaceutically acceptable vehicles additionally containing, as desired, pharmaceutically acceptable adjuvants including thickeners, preservatives, and coloring and flavoring agents.

Powder formulations can be prepared by dry blending ingredients under conditions of controlled temperature and humidity using conventional equipment. Tablet formulations can be prepared by combining the active components with tableting aids, fillers and palatability aids in a conventional manner and tableting on a conventional machine.

EXAMPLE

Relief of heartburn episodes with famotidine

The efficacy of treatments with antacid, famotidine or placebo, for relief of spontaneous heartburn episodes, was compared. Patients tested in the study had experienced a history of heartburn managed by self-medication with antacid 3 or more times per week. During a one week baseline phase of the study, patients had to have at least 3 episodes of heartburn that improved within 1 hour after a single-blind dose of antacid. Individuals with significant concurrent disease, hypersensitivity to study medication, or a contraindication to upper GI endoscopy or motility study and women who were lactating or pregnant were excluded from the study. Also excluded were patients under treatment with other investigational drugs within 1 month of entry, or who were expected to require concomitant use of other $H_2$-receptor antagonists, proton pump inhibitors, prostaglandins, or sucralfate. Concomitant medication was otherwise unrestricted.

The study compared the efficacy and safety of 5 treatments: placebo, famotidine 5 mg, famotidine 10 mg, famotidine 20 mg, and antacid. The antacid was re-compressed Gelusil® (magnesium/aluminum hydroxide), having an acid neutralizing capacity of approximately 11.0 mEq, typical of antacids used widely for heartburn relief.

Treatment was allowed as needed for heartburn up to twice daily. A pocket-size, diary card provided double-dummy test medication and space to record responses to individual doses. An open-label antacid (Wingel® magnesium/aluminum hydroxide; acid neutralizing capacity of approximately 12.3 mEq) was provided separately in the event test medication did not provide adequate relief to the patient.

For each dose of medication patients recorded their response at 1, 2 and 3 hours using the following scale:

1) completely relieved (gone)
2) better (noticeably improved)
3) unchanged (not much different)
4) worse (more severe)

Compete relief of heartburn by 1 or 2 doses of test medication without use of backup medication was considered a success.

Relief of the first heartburn episode was evaluated with additional responses at ½ hour and 1½ hours after taking the test medication. An episode was defined as ending when a score of "completely relieved" was recorded.

At the conclusion of the study, patients assessed their response to treatment over the 28-day study period as excellent, good, fair, poor, or none.

Predefined endpoints and a prioritized ordering of statistical questions were established. The patient was the experimental unit for all analyses. A sample size of 85 subjects per treatment group allowed 80% power to detect a 25% difference in the proportion of episodes relieved between placebo and active treatment (at alpha=0.05, 2-tailed test).
Results The number of heartburn episodes requiring self-medication was analyzed with a likelihood ratio test based on the Poisson distribution for counts data (Lehman: Testing Statistical Hypotheses, New York, John Wiley & Sons (1986) pp. 1–22). The proportion of episodes relieved and the proportion of episodes requiring backup antacid were calculated for each patient over the double-bind treatment period. The distributions of patient responses were divided into ordered categories to assess proportion of episodes relieved, proportion of episodes requiring backup medication, proportion of episodes requiring remediation and global evaluation. Groups were compared using a logistic regression model (SAS, PROC LOGISTIC (McCullagh, J. Royal Stat. Soc; (1980); 42 (Series B): pp. 102–142), which included factors for treatment, investigator, and covariates for the severity and number of episodes recorded during the baseline week. Time-to-relief of first episode was evaluated by survival analysis (Cox regression models) using SAS PROC PHGLM (Cox, J. Royal Stat. Soc. (1972) 34 (Series B) pp. 187–220). A supplemental analysis explicitly incorporated time to relief into the criterion for judging success. Each episode was classified into one of 4 ordered categories: 1) relief within 1 hour without backup medication 2) relief within 2 hours without backup medication 3) relief within 3 hours without backup medication 4) no relief or backup medication required. For comparison of treatment groups, each patient provided a set of four numbers indicating the number of episodes which fell into each category. The distributions of patient responses were compared using a generalized estimating equations approach which maintains the patient as the unit of analysis and adjusts for the fact that individual patients treated multiple episodes.

The reported p-values have not been adjusted for multiple comparisons. Multiplicity was addressed by calculation of the O'Brien Global Assessment statistic for the principal endpoints: proportion of episodes relieved, proportion of episodes requiring backup antacid, proportion of episodes requiring remediation (patients were permitted to take a second dose of test medication if the heartburn episode persisted for 3 or more hours after the first dose), time to relief of first episode, and global evaluation at the conclusion of the study. This calculation was performed after taking into account correlation among endpoints.

For the 565 patients studied, the median number of heartburn episodes treated per day was 0.7. Patients treated similar numbers of episodes in all 5 treatment groups during Weeks 1 and 2, and during Weeks 3 and 4. Treatment did not substantially change the tendency to develop heartburn episodes over 4 weeks.

Compared to placebo, patients assigned to receive famotidine 5 mg, famotidine 10 mg, famotidine 20 mg, and antacid reported higher proportions of episodes relieved and smaller proportions of episodes requiring backup antacid. Few episodes required remediation in any treatment group (Table 1—patient population=553). The time to relief of the first heartburn episode was significantly shorter in the famotidine 5 mg, 10 mg and antacid groups than in the placebo group. Finally, patients who received famotidine reported more favorable global evaluations than patients who received placebo. Using a per-protocol approach, statistically significant advantages favoring famotidine were identified for all 3 famotidine treatment groups. In the antacid group, patients reported numerically greater proportions of favorable responses than in the placebo group but formal comparison of the distributions did not demonstrate a statistically significant difference.

To assess whether the pattern of differences versus placebo is a result of multiple statistical tests, an O'Brien global assessment statistic was calculated for each treatment group. This statistic takes into account the numerical magnitude of the unadjusted p-values and the correlation among endpoints. The O'Brien statistic values indicate that the pattern of differences versus placebo is unlikely to have been observed by chance, supporting the conclusion that the results favoring antacid and famotidine 5 mg, famotidine 10 mg, and famotidine 20 mg versus placebo are not a statistical artifact due to multiple testing (Table 2).

An additional analysis based on all heartburn episodes was performed to assess relief at 1, 2, and 3 hours, using a definition of success that incorporates the time required to obtain complete relief. This combines all endpoints related to relief of heartburn episodes into a single endpoint. The average percentage of episodes relieved in 1, 2, or 3 hours was higher in the famotidine and antacid groups than in the placebo group.

These data were analyzed by calculating an odds ratio for relief relative to placebo using generalized estimating equations. The odds ratio expresses the chance to obtain relief relative to placebo: a value greater than 1.00 indicates that a treatment has a higher chance of providing relief than placebo. The odds ratios show statistically significant advantages versus placebo favoring famotidine 5 mg, famotidine 10 mg, and famotidine 20 mg and the reference antacid: famotidine 5 mg 1.55, p=0.003; famotidine 10 mg, 1.94 p<0.001; famotidine 20 mg, 2.13, p<0.001; antacid 1.57, p=0.003.

Patients underwent endoscopy before double-blind treatment. The presence of esophagitis was assessed endoscopically using a pre-defined grading scale (Hetzel et al., Gastroenterology (1988); 95: pp. 903–912). To determine how response was affected by the presence of esophageal erosion, heartburn relief was assessed after grouping patients according to the presence or absence of erosive esophagitis (FIG. 1A and FIG. 1B).

In patients without evidence of esophagitis, advantages versus placebo were identified favoring all treatments. The success in treating patients suffering from heartburn without esophagitis is not dose dependent, i.e., the benefit achieved by administering a 5 mg dose of famotidine to patients suffering from heartburn without esophagitis is substantially the same as the benefit achieved by administering 10 mg or 20 mg doses of famotidine.

The results demonstrate that compared to placebo, patients who received antacid documented a higher proportion of episodes relieved, a smaller proportion of episodes requiring open-label backup antacid, and a shorter time to relief. These findings show for the first time that antacid is more effective than placebo in relieving individual heartburn episodes. The data also show that, with antacid, approximately 50% of heartburn episodes were relieved within 2 hours, which is longer than clinical experience suggested. Although partial relief or improvement generally occurred by 1 hour, episodes that improved without being completely relieved were not considered successfully treated.

Famotidine was more effective than placebo in this study. Compared to placebo, patients documented a higher proportion of episodes completely relieved, a smaller proportion of episodes requiring open-label backup antacid, and a shorter time to relief. There was also a statistically significant advantage versus placebo in patient global assessments. Statistical analyses provide evidence that the profile of efficacy with famotidine and antacid is not a statistical artifact due to multiple comparisons.

The demonstrated effects are clinically relevant. Antacid was associated with a 21 percentage point increase in median proportion of episodes complete relieved. Famotidine treatment (10 mg) was associated with a 29 percentage point increase in the median proportion of episodes completely relieved. Both treatments decreased the proportion of episodes requiring backup medication. The patient global evaluations also provide evidence that the effects are relevant. Both antacid and famotidine were associated with increases in the proportion of patients assigning a good or excellent global evaluation. In the famotidine groups, this difference versus placebo reached statistical significance.

Overall, the efficacy profile of famotidine was generally similar to antacid: approximately 50% of episodes were completely relieved within 2 hours with both antacid and famotidine. The most likely explanation for this longer than expected time interval (particularly for antacid) is that complete disappearance of symptoms was required for an episode to be considered relieved. An episode in which symptoms decreased partially was not considered relieved.

TABLE 1

Efficacy Results, Episode Based Endpoints (all patients)

| Treatment | % of Episodes Relieved (Median) | % of Episodes Requiring Backup (Median) | % Patients w/No Episodes Requiring Remedication | Time to Relief of First Episode (Hours) |
|---|---|---|---|---|
| Placebo | 41 | 43 | 58 | 2.0 |
| Antacid | 62* | 32* | 66 | 1.5* |
| Fam 5 mg | 59+ | 31* | 65 | 1.5* |
| Fam 10 mg | 70*** | 26*** | 72* | 1.5* |
| Fam 20 mg | 69*** | 26*** | 69+ | 2.0 |

*p < 0.05
***p < 0.001
+0.05 ≤ p < 0.10

TABLE 2

O'Brien Global Assessment Statistic and Significance Values for Comparisons of Famotidine vs Placebo (all patients)

| | Treatment compared to placebo | | |
|---|---|---|---|
| | Famotidine 5 mg | Famotidine 10 mg | Famotidine 20 mg |
| All-Patients-Treated | 2.92(0.002) | 3.37(<0.001) | 3.27(<0.001) |
| Per-Protocol | 2.89(0.002) | 3.62(<0.001) | 3.60(<0.001) |

Legend: Calculation of O'Brien Global Assessment statistic (reference). Values of this greater than 1.96 correspond to a statistically significant difference versus placebo.

What is claimed is:

1. A method for treating a human suffering from heartburn and having no substantial esophageal erosion, comprising administering to the patient a composition comprising an amount of famotidine between about 5 mg and 10 mg sufficient to treat heartburn, wherein the composition does not contain an antacid.

2. A method of claim 1, wherein the amount of famotidine is about 5 mg.

3. A method of claim 1, wherein the amount of famotidine is about 10 mg.

* * * * *